(12) United States Patent
Norvell

(10) Patent No.: US 10,500,101 B1
(45) Date of Patent: Dec. 10, 2019

(54) WATERPROOF CAST LINER SYSTEM AND METHOD OF USE

(71) Applicant: Jean Norvell, New Castle, DE (US)

(72) Inventor: Jean Norvell, New Castle, DE (US)

( * ) Notice: Subject to any disclaimer, the term of this patent is extended or adjusted under 35 U.S.C. 154(b) by 0 days.

(21) Appl. No.: 16/260,602

(22) Filed: Jan. 29, 2019

Related U.S. Application Data

(60) Provisional application No. 62/739,804, filed on Oct. 1, 2018.

(51) Int. Cl.
- *A61F 5/00* (2006.01)
- *A61F 13/04* (2006.01)
- *A61F 15/00* (2006.01)
- *A61F 13/00* (2006.01)

(52) U.S. Cl.
CPC .......... *A61F 13/041* (2013.01); *A61F 15/004* (2013.01); *A61F 2013/00889* (2013.01)

(58) Field of Classification Search
CPC .......... A61F 13/04; A61L 15/00; A61L 15/004
USPC .......................................................... 602/3
See application file for complete search history.

(56) References Cited

U.S. PATENT DOCUMENTS

| | | | |
|---|---|---|---|
| 3,802,424 A | 4/1974 | Newell | |
| 4,194,041 A | 3/1980 | Gore et al. | |
| 4,494,536 A | 1/1985 | Latenser | |
| 5,016,622 A * | 5/1991 | Norvell | A61F 13/041 602/20 |
| 5,480,455 A | 1/1996 | Norvell | |
| 5,527,265 A * | 6/1996 | McKeel | A61F 5/05841 428/71 |
| 5,718,674 A * | 2/1998 | Penrose | A61F 13/0273 602/46 |
| 5,728,169 A * | 3/1998 | Norvell | A61F 2/7812 2/22 |
| 5,817,038 A * | 10/1998 | Orange | A61F 13/041 602/3 |
| 5,944,675 A | 8/1999 | Bequet-Sharber et al. | |
| 6,126,621 A * | 10/2000 | Aceves | A61F 13/041 128/878 |
| 6,880,173 B2 | 4/2005 | Green | |
| 6,981,955 B2 | 1/2006 | Schultze et al. | |
| 7,348,697 B2 | 3/2008 | Kreitzer | |

(Continued)

FOREIGN PATENT DOCUMENTS

WO  WO-9310732 A1 * 6/1993 ........... A61F 13/041

*Primary Examiner* — Kim M Lewis
(74) *Attorney, Agent, or Firm* — Invention To Patent Services; Alex Hobson

(57) ABSTRACT

A waterproof cast liner is formed by inverting a waterproof cast sleeve over a padding material and sealing the inner and outer layers together to produce a waterproof cast. The padding material is retained within the waterproof enclosure formed by the inverted and seal liner and a rigid material is configure around the outer layer of the inverted sleeve and the limb to form a waterproof cast. A waterproof cast sleeve may have an appendage conduit that branches from the sleeve conduit to enable an appendage such as a thumb or finger to extend out from the waterproof cast. The inner and outer layer of the inverted sleeve or waterproof liner are sealed together to produce a waterproof enclosure for the padding material. The seal may include a thermal seal or adhesive and the rigid material of the cast may form an adhesive for the seal.

21 Claims, 7 Drawing Sheets

(56) References Cited

U.S. PATENT DOCUMENTS

| | | | |
|---|---|---|---|
| 7,465,283 B2 * | 12/2008 | Grim | A61F 5/01 |
| | | | 602/5 |
| 8,430,829 B1 | 4/2013 | Marchetti | |
| 9,801,750 B2 | 10/2017 | Thompson | |
| 10,039,653 B2 | 8/2018 | Kelley et al. | |
| 2005/0020949 A1 * | 1/2005 | Switzer | A61F 15/008 |
| | | | 602/3 |
| 2007/0073201 A1 * | 3/2007 | Campagna | A61F 13/041 |
| | | | 602/8 |
| 2009/0113591 A1 * | 5/2009 | Deutsch | A41D 13/08 |
| | | | 2/16 |
| 2012/0203152 A1 * | 8/2012 | Thompson | A61F 5/01 |
| | | | 602/3 |

\* cited by examiner

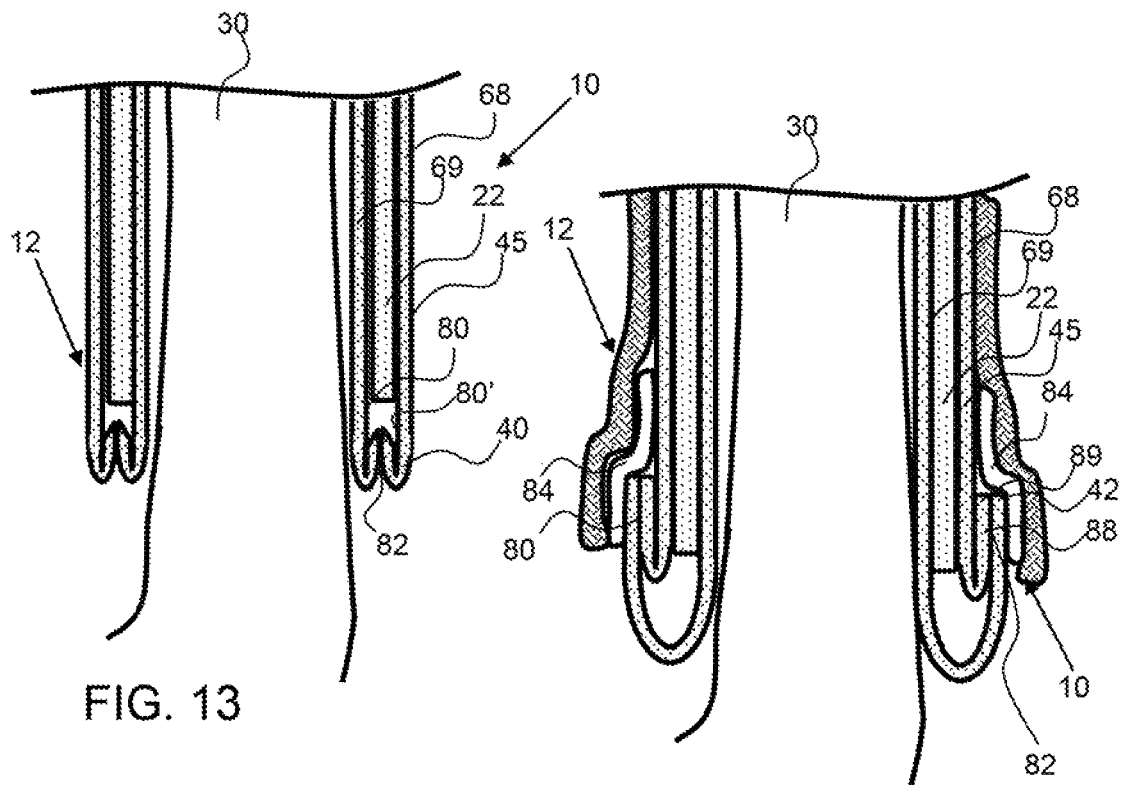
FIG. 13
FIG. 14
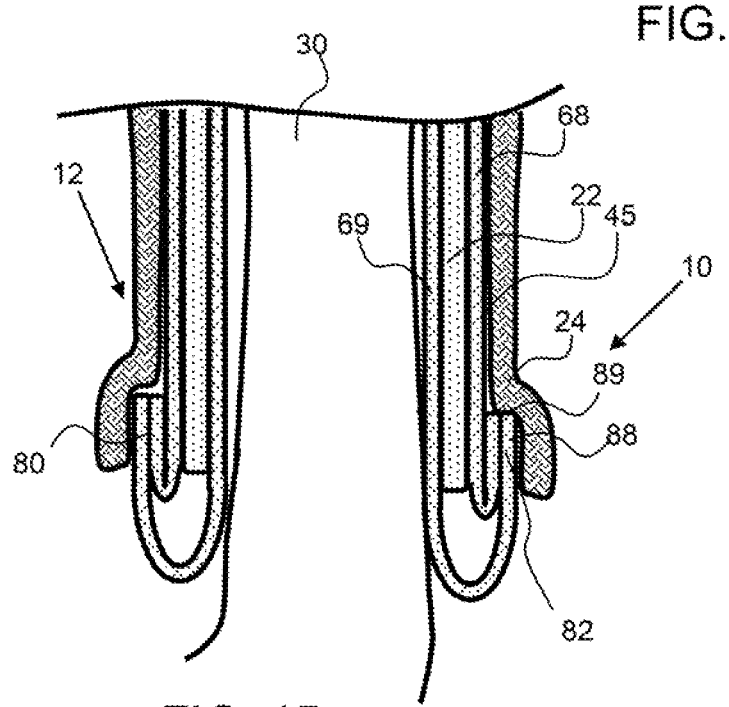
FIG. 15

WATERPROOF CAST LINER SYSTEM AND METHOD OF USE

FIELD OF THE INVENTION

This application claims the benefit of priority to U.S. provisional patent application No. 62/739,804, filed on Oct. 1, 2018; the entirety of which is hereby incorporated by reference herein.

BACKGROUND OF THE INVENTION

Field of the Invention

The present invention is directed to a waterproof cast liner system and a method of using a waterproof cast liner which produces a waterproof cast, but also utilizes the same wrapping techniques as used for non-waterproof casts, which is the standard employed by medical professionals.

Background

There are limited waterproof cast options. There are waterproof bags that can cover the entire extended end of a person's broken limb and which are used for showering. These bags are not an effective waterproof seal. If the limb is submerged, water pressure can break the seal between the bag and the person's limb. Alternatively, a waterproof padding liner material is available that can be applied over the broken limb, such as by wrapping. The fiberglass cast can then be layered over this waterproof material. However, this padded material is not amenable to normal wrapping techniques which is the standard for non-waterproof casting materials. The padding material does not sufficiently elongate, a necessity if it is to fit muscle curvature as well as the curves at thumb and wrist. Therefore, several cuts are needed within the product itself in order for it to be able to fold and bend upon itself to fit these curves. Additionally, as the technicians apply the padding close to the elbow area, the padding may have to be cut several times, and new pieces reapplied in order to adjust to the curvature of the muscles and bone below the elbow. Use of these materials requires additional training for technicians to ensure that the new materials are deployed correctly, have sufficient padding in the required areas, and do not exert too much pressure on the limb. A need exists for an improved waterproof cast liner system, which overcomes the limitations described. A further need exists for a waterproof cast liner which is amenable to the same or similar waterproof techniques as those used for conventional non-waterproof casts, which is the standard employed by medical professionals.

SUMMARY OF THE INVENTION

The invention is directed to a waterproof cast liner system and a method of using a waterproof cast liner to produce a waterproof cast. An exemplary waterproof cast liner comprises an inverted waterproof cast sleeve that extends around a padding material. An exemplary waterproof cast sleeve has a sleeve conduit for the insertion of a person's broken limb, such as an arm or leg. The waterproof cast sleeve extends over the limb and extends from the end of the limb to an extended end. A padding material, such as a hydrophilic padding layer, may then be applied around the broken limb and over the portion of the waterproof cast sleeve covering the person's limb. After the padding layer is applied, the waterproof cast sleeve can then be inverted back over the padding layer to produce a waterproof cast liner around the padding material. The extended end is pull back over the inner layer of the waterproof cast sleeve and a seal is produced between the inside and outside layers to produce a waterproof enclosure around the padding layer.

In an exemplary embodiment, the waterproof cast sleeve comprises an appendage sleeve that forms a branch conduit with the sleeve conduit. The insertion end and extended end of the appendage sleeve open into the sleeve conduit. An appendage sleeve may be used for the insertion of a finger, thumb or toe, for example.

An exemplary waterproof cast sleeve comprises a waterproof layer, or a waterproof material that has a water entry pressure of about 16.9 kPa or 1 psi or more, when exposed to said water entry pressure for one minute. In an exemplary embodiment, a waterproof cast sleeve is also permeable to gases which will allow perspiration to pass through the waterproof cast sleeve. An exemplary waterproof cast sleeve comprises a permeable membrane, such as expanded polytetrafluoroethylene (ePTFE), membrane. An exemplary ePTFE membrane is available from W.L. Gore and Associates, Inc, Newark, Del. An ePTFE membrane may comprises a support layer, such as a fabric or a moisture vapor transmission layer, such as a thin urethane layer. A waterproof cast sleeve may be a composite of a waterproof layer and a support layer and/or a moisture vapor transmission layer. The support layer or moisture vapor transmission layer may be configured as the inside layer of the sleeve conduit.

An exemplary support layer may be a film of polymer or a fabric, such as a woven or non-woven fabric, and the like. The support layer may prevent stretching of the waterproof material and may also be a waterproof material or be hydrophobic, wherein water does not wet the surface of the support layer material.

An exemplary moisture vapor transmission layer may be a polymeric material that has high moisture vapor transmission rates; sufficient to enable perspiration to pass through the waterproof cast sleeve at an effective rate for comfort. An exemplary moisture vapor transmission layer may have no bulk flow of air therethrough and may be a thin film of polymer, such as urethane or silicone. No bulk flow of air is defined as a Gurley value of 500 seconds or more as measured with a Gurley Model 4340 Automatic Densometer, available from Gurley Precision Instruments, Troy, N.Y.

The waterproof cast sleeve forms an enclosure around a padding material with the application of a seal between the inner layer and outer layer of the liner, proximal to the insertion end. An exemplary seal between the inner layer an outer layer of the waterproof cast liner may comprise a thermal bond, an adhesive, an adhesive tape, a sleeve and the like. In an exemplary embodiment, the inner and outer layers are bonded by a thermal bond, wherein a portion of the inner layer and/or outer layer are melted to produce a bond and seal. For example, the moisture vapor transmission layer may be a thermoplastic material and may be melted to produce a thermal bond with the moisture vapor transmission layer of the opposing layer, with a support layer or with the waterproof layer. In some cases, the insertion end and/or the extended end may be folded back to enable an effective thermal bond. In an exemplary embodiment, an adhesive is configured between the inner and outer layers of the waterproof cast liner to produce a waterproof seal. An adhesive may be liquid adhesive, or an adhesive tape or strip that extends from one layer to the other layer to produce a waterproof seal. An adhesive tape may extend from the inside layer over the insertion end to the outside layer, for example.

In an exemplary embodiment, a padded liner is configured around the insertion end of the waterproof cast liner. The padded liner may extend out from between the person's limb and the cast liner and fold around the seal end to provide some padding for the end of the cast. An exemplary padded liner may comprise a resilient material that can be deformed or compressed and then rebound to substantially an original thickness after compression. An exemplary padded liner or resilient material thereof may comprise fabric, foam or an elastomeric material. The padded liner may be adhered to the inside layer of the waterproof cast sleeve prior to producing the waterproof cast liner or it may be configured in place during the casting procedure. A padded liner may be a waterproof material or a hydrophobic material that does not absorb water. A padded liner may extend about 50 mm or more under the insertion end of the waterproof cast sleeve and may fold around the insertion end and be attached to the waterproof cast, such as to the waterproof cast sleeve or to the rigid material.

An exemplary waterproof cast sleeve may be used to produce a waterproof cast. As detailed herein, a person's limb may be inserted into the waterproof cast sleeve conduit through the insertion end to cover a portion of the person's limb with the inner layer of the waterproof cast sleeve. A padding material, such as gauze, may then be configured around the persons limb and over the inner layer to produce a padding layer. The extended end of the waterproof cast sleeve may then be inverted back over the person's limb and the inner layer of the waterproof cast sleeve to produce a waterproof cast liner around the padding material, wherein the padding material is configured between the inner and outer layers of the waterproof cast sleeve. A seal can be produced between the inner and outer layers proximal the insertion end to produce a waterproof enclosure around the padding layer. A rigid layer, such as a fiberglass material or composite, may then be applied around the outer layer of the waterproof cast liner to produce a waterproof cast. In an exemplary embodiment, the waterproof cast sleeve comprises an appendage sleeve that branches from the waterproof cast sleeve conduit to create an appendage conduit that loops over a portion of the sleeve conduit. The insertion end and the extended end of the appendage conduit open into the sleeve conduit.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

FIG. 13 shows a sectional view of an exemplary waterproof cast sleeve system wherein the insertion end and extend end of the waterproof cast sleeve are inverted toward each other to produce a seal.

FIG. 14 shows the inner layer of the waterproof cast sleeve folded back over the outside of the outer layer of the waterproof cast sleeve to produce a cuff and an adhesive tape configured the cuff and extending onto the outer surface of the inverted outer layer of the waterproof cast sleeve.

FIG. 15 shows the inner layer of the waterproof cast sleeve folded back over the outside of the outer layer of the waterproof cast sleeve to produce a cuff and the rigid layer configured over the cuff and extending onto the inverted outer layer to produce a waterproof cast.

Figure 1:
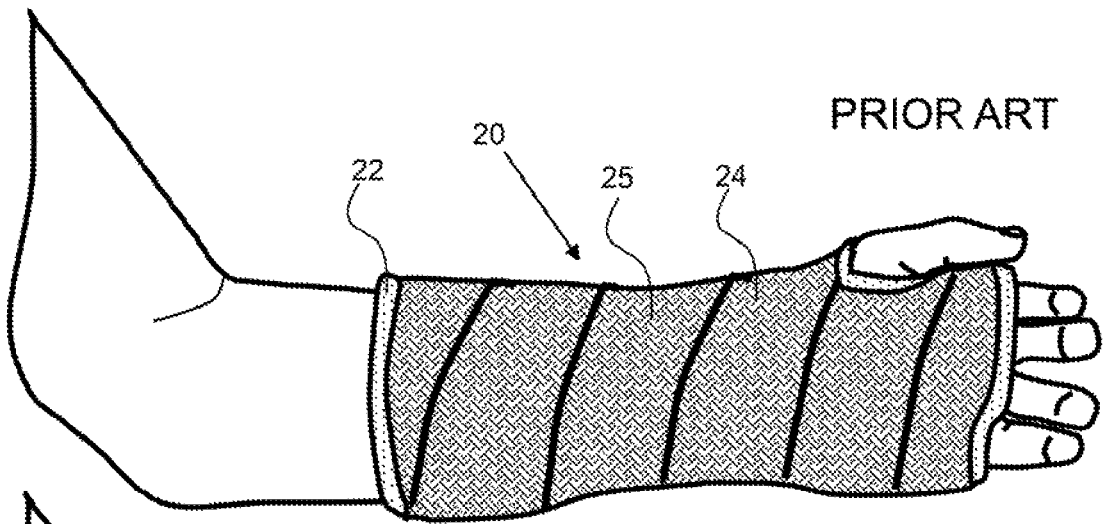
FIG. 1 shows a conventional cast configured over a person's arm and having a rigid layer over a hydrophilic padding layer.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Figure 2:
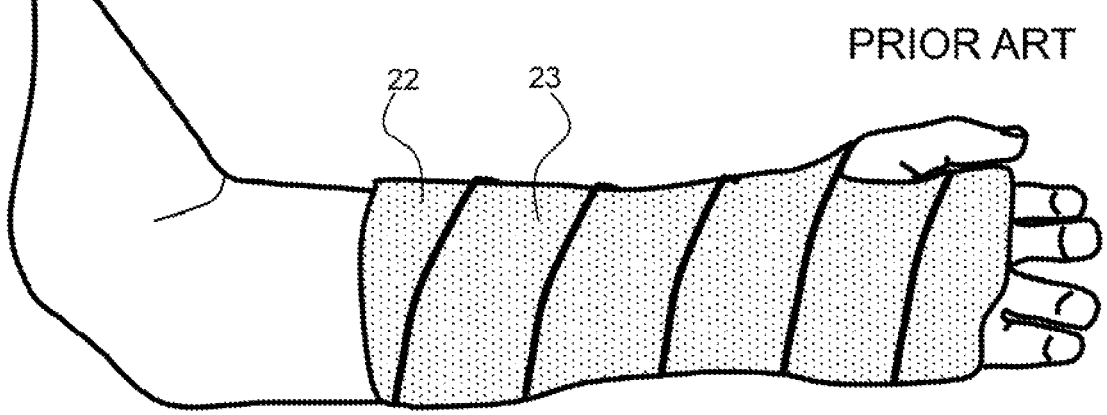
FIG. 2 shows a hydrophilic padding layer configured over a person's arm.
Figure 3:
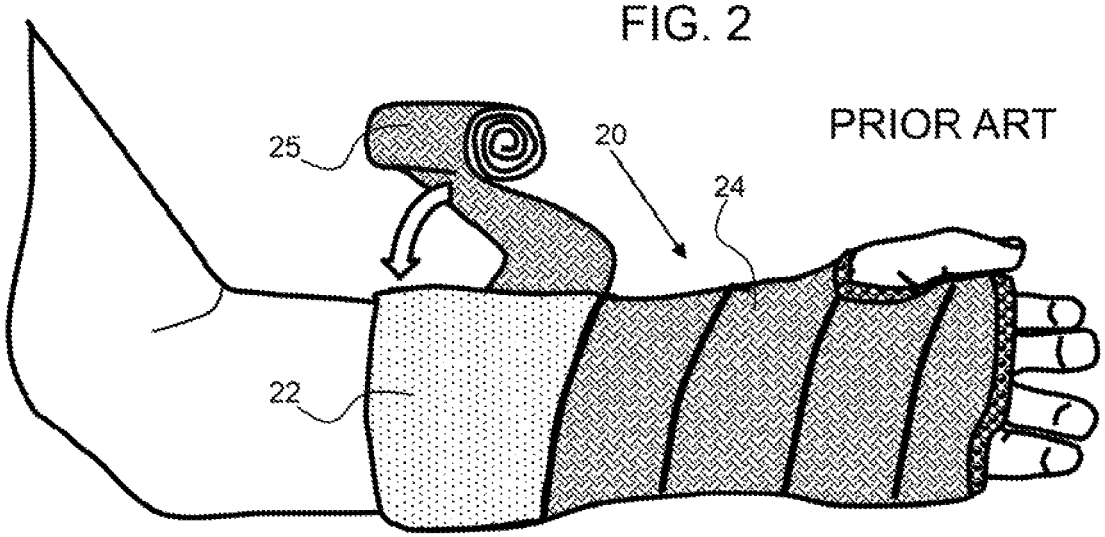
FIG. 3 shows the rigid layer, such as fiberglass, being configured over a hydrophilic padding layer to produce a conventional cast, as shown in FIG. 1.

Referring now to FIGS. 1 to 3, a conventional cast 20 is configured over a person's arm and has rigid layer 24 over a hydrophilic padding layer 22 comprising hydroscopic padding 23. As shown in FIG. 2, a hydrophilic padding layer 22 is configured over a person's arm. The hydrophilic or non-waterproof padding material 23 may be elongated, thereby making it easier for the clinician to wrap the padding around the thumb. As shown in FIG. 3, the rigid layer 24, such as fiberglass 25, is being configured over the hydrophilic padding 22 layer to produce a conventional cast 20. The fiberglass material is wet and supple during application and when it dries it becomes a rigid layer.

Figure 4:
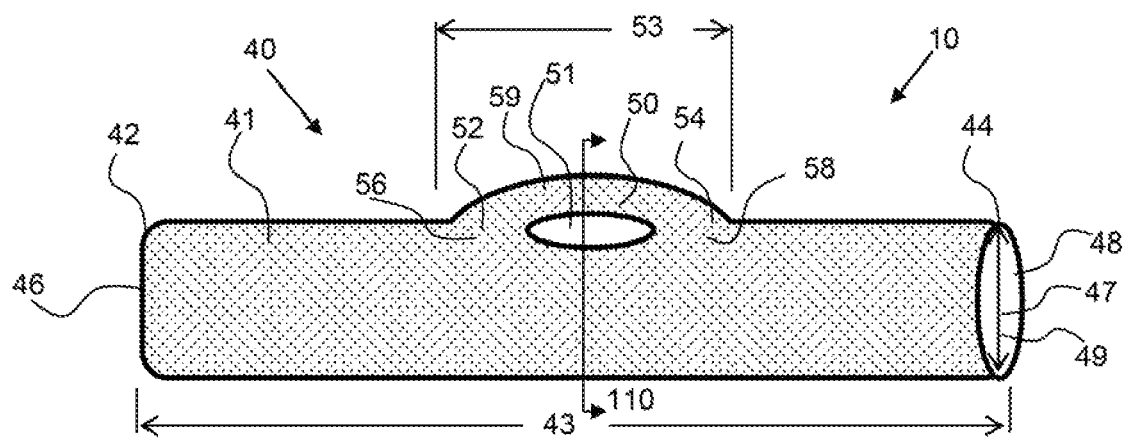
FIG. 4 shows an exemplary waterproof cast sleeve that is configured to be inverted to produce a waterproof enclosure for the padding layer of a cast.

Referring now to FIGS. 4 to 9, an exemplary waterproof cast sleeve system utilizes an inverting waterproof cast sleeve 40 that produces a waterproof enclosure for the padding layer of a cast. As shown in FIG. 4, an exemplary waterproof cast sleeve has a length 43 from an insertion end 42 to an extended end 44. The waterproof cast sleeve forms a conduit 49 having a diameter 47. The exemplary waterproof cast sleeve 40 comprises a waterproof material 41, which may have a high moisture vapor transmission rate to allow perspiration from a person's skin to pass through the waterproof material. The waterproof cast sleeve has an insertion end opening 46 for receiving a person's limb and an extend end opening 48 that is inverted back towards the insertion end to produce an inner and outer layer of the inverted waterproof cast sleeve. This exemplary waterproof cast sleeve has an appendage sleeve 50 having a length 53 from an insertion end 52 and an extended end 54. An appendage seal aperture 51 is configured between the cast sleeve conduit 49 and the appendage conduit 59. The appendage sleeve may have a diameter that is much smaller than the diameter 47 of the waterproof cast sleeve, such as ½ or less, about ⅓ or less, about ¼ or less, about 1/10 or less and any range between and including the values provided.

Figure 5:
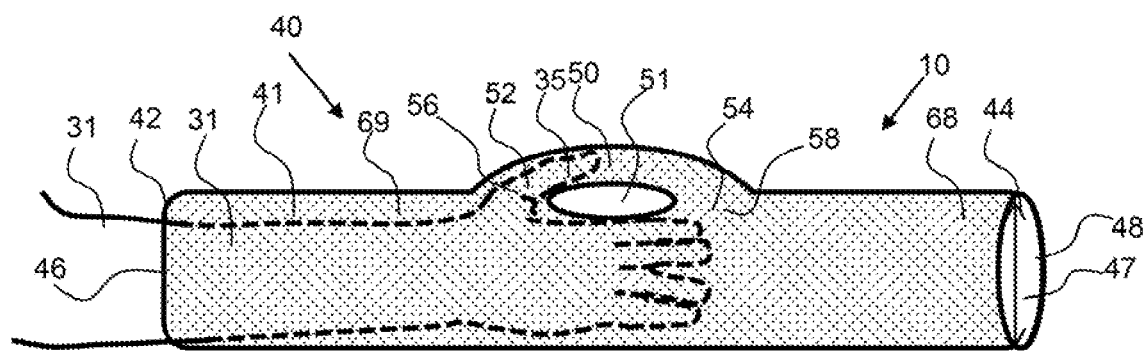
FIG. 5 shows a person's hand inserted into the waterproof cast sleeve shown of FIG. 4, wherein the person's thumb extends into the appendage sleeve.

As shown in FIG. 5, a person's arm 31 is inserted through the insertion end opening 46 of the waterproof cast sleeve and their thumb 35 is inserted into the insertion end opening 56 of the appendage sleeve 50, or into the insertion portion of the waterproof cast sleeve 40. The thumb sleeve conduit 59 extends from the insertion end opening 46 to the extended end opening 58. The appendage conduit 59 couples with the cast sleeve conduit 49. It is to be understood that the extended portion of the waterproof cast sleeve may be rolled up in an inverted manner and then subsequently unrolled back over the person's limb after the padding layer is configured around the person's limb. This inverted roll may be a more manageable configuration for the clinician or doctor applying the cast.

Figure 6:
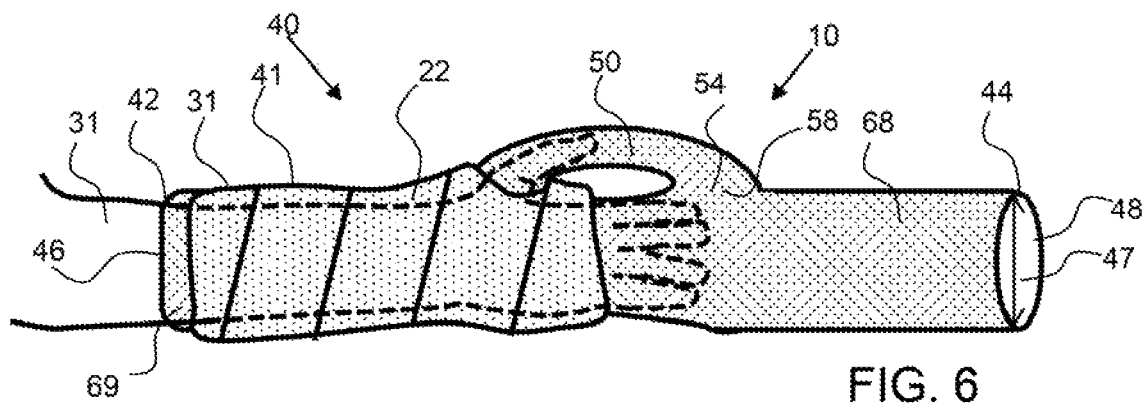
FIG. 6 shows a padding layer configured around the person's arm and over the inner layer of the waterproof cast sleeve shown in FIG. 5.

As shown in FIG. 6, a padding layer 22 has been applied over the insertion portion of the waterproof cast sleeve 40. The waterproof cast sleeve 40 extends out from the padding layer on the extended end. Also note than the padding material is configured through the appendage seal aperture 51 and around the person's hand.

Figure 7:
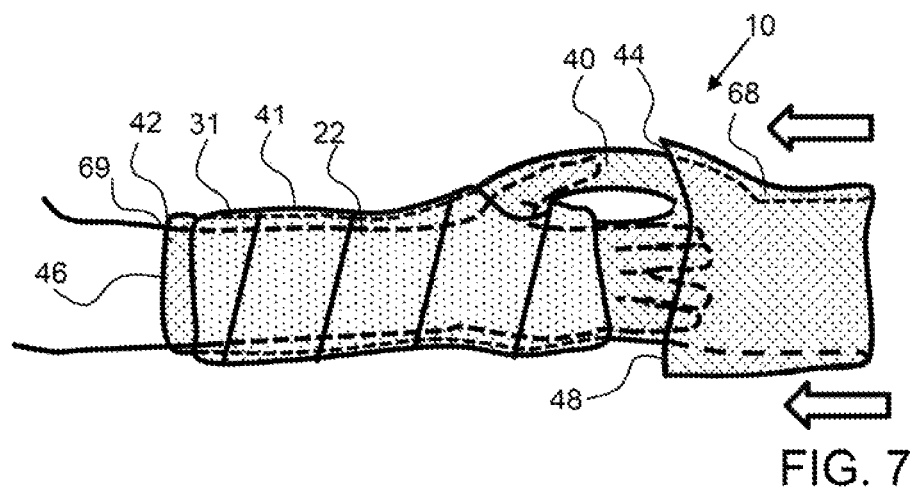
FIG. 7 shows the outer layer of the waterproof cast sleeve being inverted back over the person's arm and thumb and over the padding layer and the inner layer of the waterproof cast sleeve to enclose the padding layer in the waterproof cast sleeve.
Figure 8:
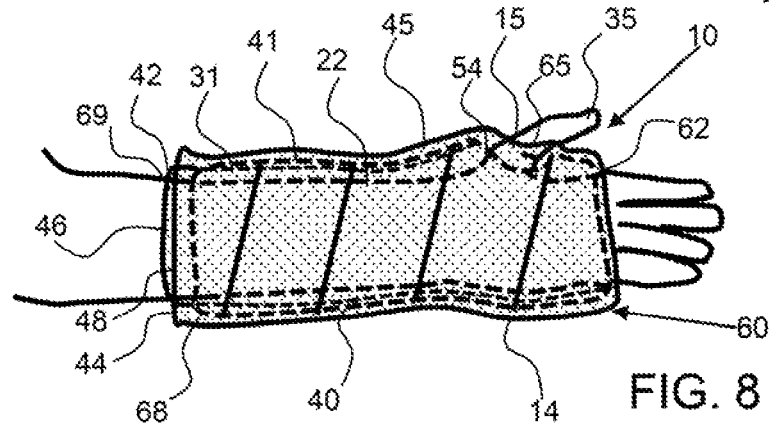
FIG. 8 shows the waterproof cast sleeve configured around the padding layer with the extended end of the waterproof cast sleeve inverted back to the insertion end of the waterproof cast sleeve to produce an inverted waterproof cast sleeve.

As shown in FIG. 7, the waterproof cast sleeve 40 is being inverted, wherein the extended end 44 is being inverted or pulled back over the insertion portion of the waterproof cast sleeve and over the padding material. As shown in FIG. 8, the inverted portion of the inverted waterproof cast sleeve 45 forms an inverted sleeve 60, or waterproof cast liner 14 around the padding layer 22, wherein the padding layer is configured between the outer layer 68 and the inside layer 69 of the inverted waterproof cast sleeve. The padding layer is configured in an enclosure between the inside layer and outside layer of the waterproof cast sleeve and is protected from contact with liquid. The inverted portion of the inverted waterproof cast sleeve extends from the inverted end 62 to the extended end 44, which is now proximal to the insertion end 42 of the waterproof cast sleeve. The person's thumb 35 extends out from the appendage sleeve 50 or appendage conduit 59. The inverted end 65 of the appendage sleeve forms a cuff, or an appendage liner 15 around the person's thumb 35. The appendage sleeve is also inverted, wherein the extended end 54 of the appendage sleeve is inverted back over the appendage sleeve. Note that the inverted end of the waterproof sleeve 62 and the inverted end of the appendage sleeve prevent liquid contact with the padding layer as it produces a continuous liner, or seamless liner, from the insertion end to the inverted extended end. These inverted ends do not have seams and produce a durable waterproof cuff around the hand and thumb.

Figure 9:
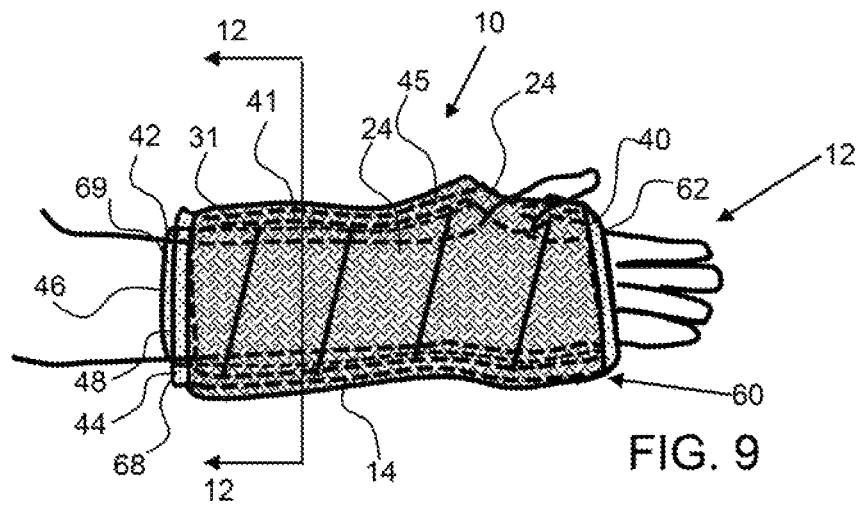
FIG. 9 shows a rigid layer configured over the outer layer of the inverted waterproof cast sleeve to produce a waterproof cast.

As shown in FIG. 9, a rigid layer 24 is configured over the outer layer 68 of the inverted waterproof cast sleeve 45. The rigid material also extends around the person's thumb and around their had to form a contiguous rigid body around the person's limb, a waterproof cast 12.

Figure 10:
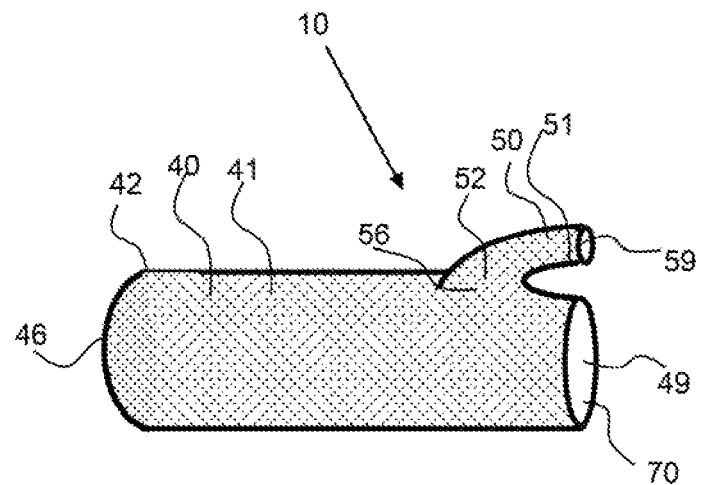
FIG. 10 shows a cut-away view along line 110 of FIG. 8 of an exemplary waterproof cast sleeve having an appendage conduit and the sleeve conduit.
Figure 11:
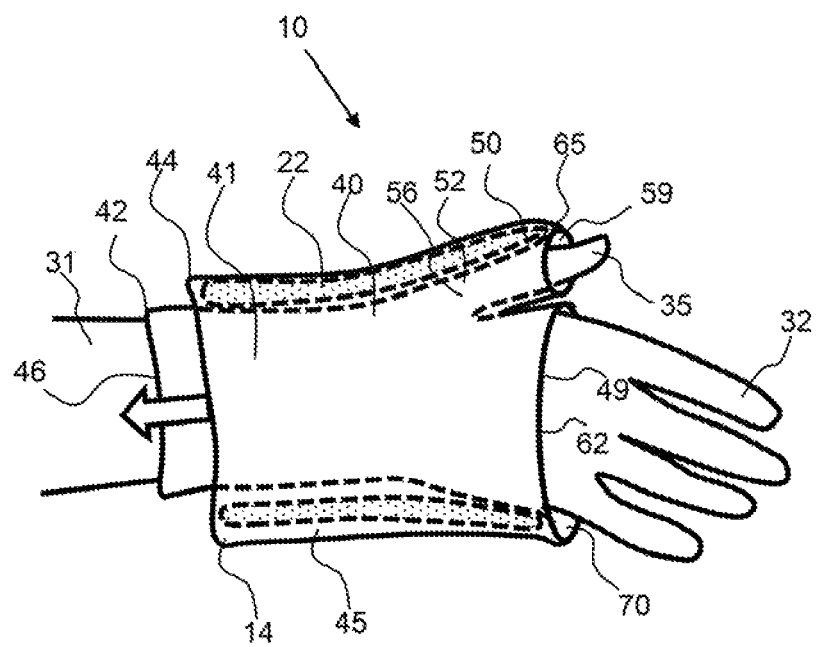
FIG. 11, shows an exemplary waterproof cast liner system with the waterproof cast sleeve inverted back over the end of the thumb and the person's hand.

Referring FIGS. 10 and 11, an exemplary waterproof cast sleeve 40 has a cast sleeve conduit 49 extending from an insertion end 42 to an extended end 44 for the insertion of a person's limb, such as the arm 31 as shown in FIG. 11. The person's thumb 35 extends into the appendage sleeve 50 through the appendage insertion end opening 56. The insertion end opening of the appendage sleeve opens into the sleeve conduit 49. As shown in FIG. 11, the person's hand 32 is exposed as the waterproof cast sleeve 40 is inverted back toward the insertion end 42 to produce a waterproof cast liner 14 around the padding layer 22. The extended end 44 is inverted back over the padding layer 22 to expose the thumb and hand and to create a waterproof liner around the padding layer. The inverted end 62 of the sleeve conduit 49 and the inverted end 65 of the appendage sleeve 50 are folded or inverted waterproof material 41 requiring no seams.

Figure 12:
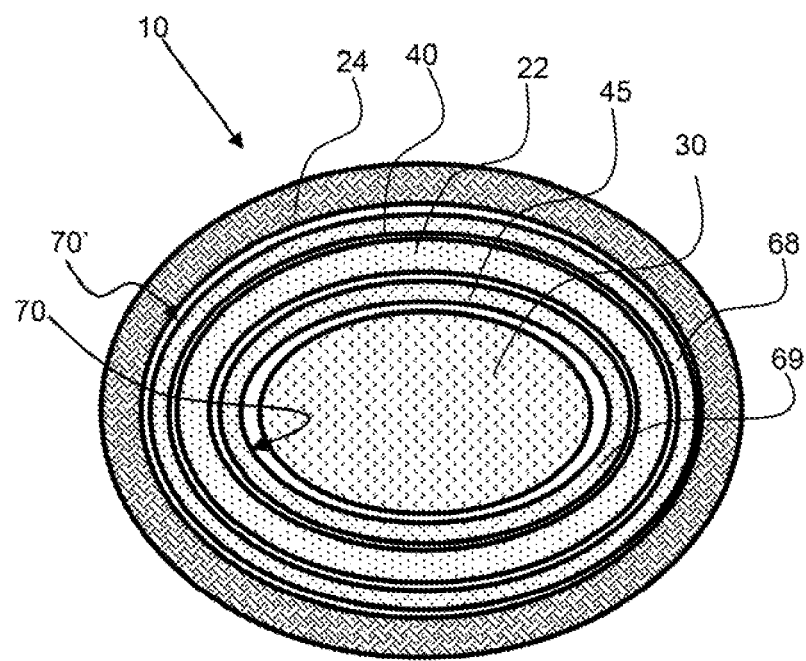
FIG. 12 shows a cross-sectional view of the waterproof cast sleeve system taken along line 12-12 of FIG. 9, and shows the padding layer between the inner and outer layers of the waterproof cast sleeve and the rigid layer configured around the outside of the outer layer of the waterproof cast sleeve.

As shown in FIG. 12, the waterproof cast sleeve system 10 forms an enclosure around the padding layer 22, wherein the padding layer is configured between the inner layer 69 and outer layer 68 of the inverted waterproof cast sleeve 45. The inner layer is adjacent the person's limb 30, such as their arm or leg and the outer layer is adjacent the rigid layer 24. The inside surfaces 70 of the insertion portion, or inner layer 69 of the waterproof cast sleeve 40 is against, or faces, the person's limb and inside surface 70' of the inverted portion, or outer layer 68 of the waterproof cast sleeve faces the rigid layer.

Referring now to FIGS. 13 to 16, a water proof cast 12 comprises a seal 82 formed between the inner layer 69 and outer layer 68 of the inverted waterproof cast sleeve 45. As shown in FIG. 11, the insertion end 42 and extend end 44 of the waterproof cast sleeve are inverted toward each other to produce a seal by an adhesive 80 on the inside surface of the waterproof cast sleeve 40. As described herein, an exemplary waterproof cast sleeve 40 may comprise a heat or moisture activated adhesive. Heat may be applied to the inverted inner and outer layers to cause the adhesive to form a seal 82, for example. Also, a seal may be formed by the application of heat to cause a portion of the waterproof cast sleeve to melt to form an adhesive bond.

As shown in FIG. 14, the inner layer 69 of the inverted waterproof cast sleeve 45 is folded back over the outside of the outer layer 68 to form a cuff 88 having an extended cuff end 89. An adhesive tape 84 is configured over the insertion end 42 of the inner layer or over the extended cuff end 89 and extends onto over the outer layer to form a seal 82. Note that this seal may be configured before the rigid layer is applied and the rigid layer may extend over at least a portion of the adhesive tape 84. Also note that an adhesive 80 may be configured between the inner and outer layers of the inverted waterproof cast sleeve in the cuff area where the outside surfaces are in contact with each other. Again, this adhesive 80 may be activated by heat or moisture, or may be applied before the inner and outer layers are configured into the cuff.

As shown in FIG. 15, the inner layer 69 of the inverted waterproof cast sleeve 45 is folded back over the outside of the outer layer 68 to form a cuff 88 having an extended cuff end 89. The rigid layer 24 is configured over the insertion end 42 of the inner layer, or over the extended cuff end 89 and extends over the outer layer to form a seal 82. The inner layer and outer layer may be retained in position by the adhesive tape 84. Note that an adhesive 80 may be configured between the inner and outer layers of the inverted waterproof cast sleeve in the cuff area where the outside surfaces are in contact with each other. Again, this adhesive 80 may be activated by heat or moisture, or may be applied before the inner and outer layers are configured into the cuff.

Figure 16:
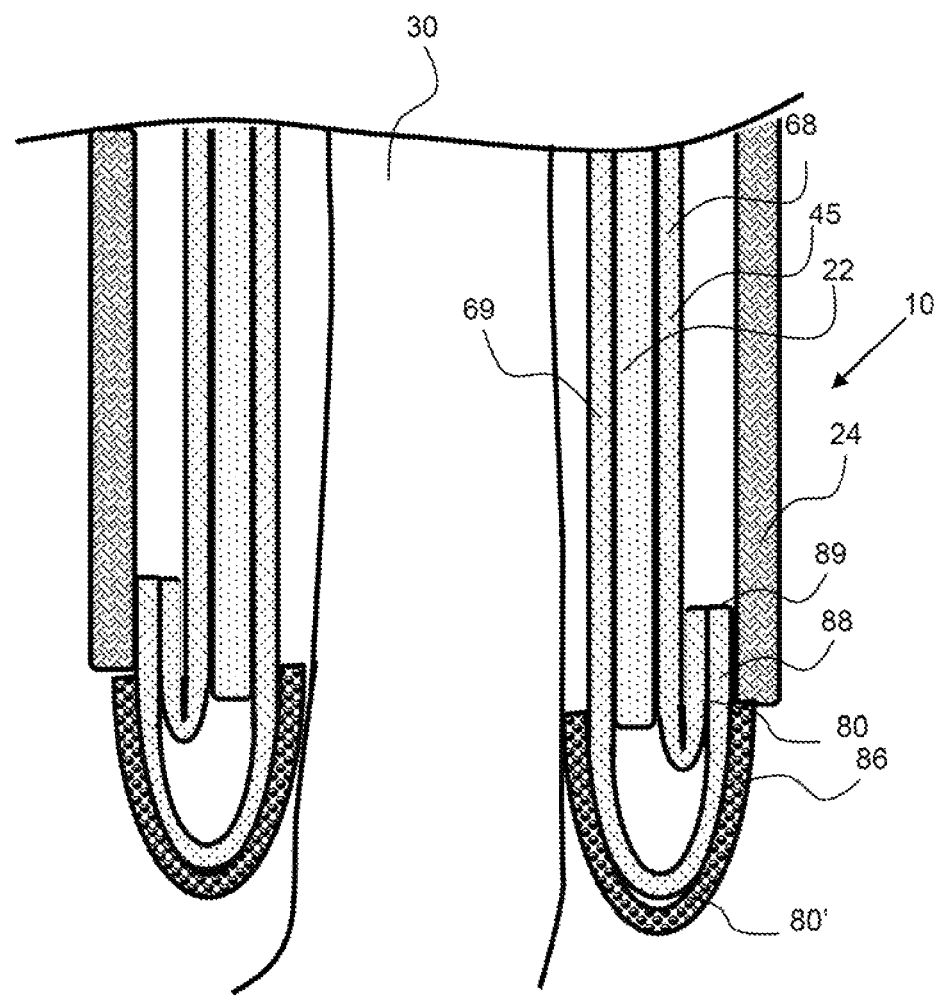
FIG. 16 shows the inner layer of the waterproof cast sleeve folded back over the outside of the outer layer of the waterproof cast sleeve to produce a cuff and the rigid layer configured over the cuff and extending onto the inverted outer layer to produce a waterproof cast and a padded liner inverted from between the inner layer or the waterproof cast sleeve and the person's limb to the outside of the cuff.

As shown in FIG. 16, the inner layer 69 of the inverted waterproof cast sleeve 45 is folded back over the outside of the outer layer 68 of the inverted waterproof cast sleeve to form a cuff 88 having an extended cuff end 89. The rigid layer 24 is configured over the extended cuff 89 and extends over the outer layer. A padded liner 86 is inverted from between the inner layer 69 of the waterproof cast sleeve and the person's limb 30 to the outside of the cuff 88. The padded liner may be a sleeve that is placed over the person's limb and configured in position with respect to the insertion end of the waterproof cast sleeve 40, or it may be attached to the waterproof cast sleeve prior to insertion of the person's limb. The padded liner may protect the person's limb from pressure caused by the end of the cast and particularly the end of the rigid layer 24. The padded liner may extend under the rigid layer or under an adhesive tape. Also, an adhesive 80' may be configured between the padded liner and the inside layer to secure the padded liner to the inside layer.

Figure 17:
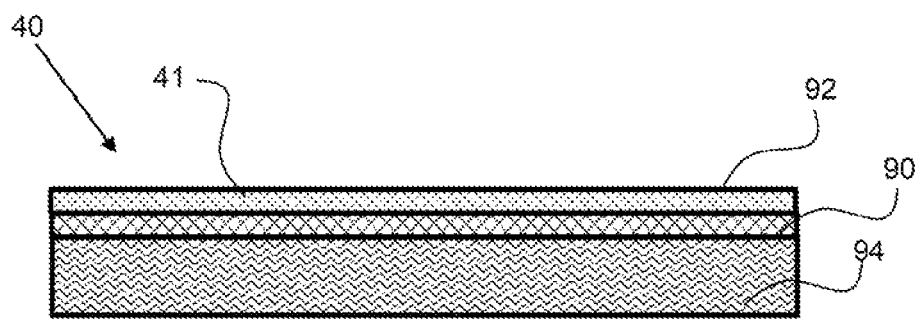
FIG. 17 shows a cross-sectional view of an exemplary waterproof sleeve that is a waterproof material comprising a membrane, a moisture vapor transmission layer and a support material, such as a fabric.

As shown in FIG. 17, an exemplary waterproof cast sleeve 40 is a waterproof material 41 that prevents water penetration through the material up to at least about 6.9 kPa or 1 psi of water pressure. The exemplary waterproof cast sleeve comprises a membrane 90, a moisture vapor transmission layer 92 and a support material 94. As described herein the membrane may have pores such as micropores with a mean pore diameter of no more than 5 microns, and may be an expanded fluoropolymer, such as an ePTFE membrane as described herein. The membrane may be air permeable but the pores may be small enough to resist water penetration through the membrane up to about 6.9 kPa or 1 psi or more. An exemplary moisture vapor transmission layer may be a thin layer of a polymer that has high moisture vapor transmission rates, such as a urethane or silicone, for example. An exemplary moisture vapor transmission layer may have no bulk flow of air therethrough, as it may be a solid film layer. An exemplary support material may be a woven or non-woven fabric, for example. The moisture vapor transmission layer may be configured as an inside surface or in some embodiment, an outside surface of a waterproof cast sleeve It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A waterproof cast liner system comprising:
   a) an inverted waterproof cast sleeve comprising:
      i) an insertion end having an insertion end opening;
      ii) an extended end having an extended end opening;
      iii) a sleeve conduit extending from the insertion end opening to the extended end opening; said sleeve conduit having an inside surface and an outside surface;
   wherein the inverted waterproof cast sleeve is configured for placement over a limb with the insertion end configured to extend around said limb with the extended end inverted back over the outside surface of the sleeve conduit to form a waterproof cast liner comprising:
      an outer layer of the inverted sleeve;
      an inner layer of the inverted sleeve; and
      an inverted end;
   wherein the outer layer and inner layer are configured to overlap each other over to form said waterproof cast liner.

2. The waterproof cast liner system of claim 1, further comprising a padding material between the inner layer and outer layer of the inverted waterproof cast liner.

3. The waterproof cast liner system of claim 2, wherein the padding material is hydrophilic.

4. The waterproof cast liner system of claim 1, further comprising a seal between the inner layer and outer layer to produce a waterproof enclosure between the inner layer and outer layer.

5. The waterproof cast liner system of claim 4, wherein the seal extends between the insertion end and the inverted extended end.

6. The waterproof cast liner system of claim 4, wherein both the inner layer and outer layer are inverted outward over the outer layer to produce a cuff and wherein the seal is configured between the inner layer and outer layer in said cuff.

7. The waterproof cast liner system of claim 6, wherein the cuff has an extended cuff end, and wherein the seal comprises an adhesive that extends from an outside surface of the outer layer over the extended cuff end to produce a seal.

8. The waterproof cast liner system of claim 7, wherein the adhesive is an adhesive tape.

9. The waterproof cast liner system of claim 4, wherein the adhesive is a cast rigid layer.

10. The waterproof cast liner system of claim 9, wherein the cast rigid layer comprises fiberglass and forms the rigid layer of a waterproof cast.

11. The waterproof cast liner system of claim 1, further comprising an appendage sleeve that is contiguous with the sleeve conduit and comprises:
   a) an insertion end having an insertion end opening;
   b) an extended end having an extended end opening;
   c) an appendage sleeve conduit extending from said insertion end opening to the extended end opening of the appendage sleeve; having an inside surface and an outside surface;
      wherein the insertion end opening and the extended end opening of the appendage sleeve are within the sleeve conduit; and
      wherein the appendage sleeve conduit is inverted back over a portion of an extended end of an appendage to expose said extended end of the appendage.

12. A waterproof cast liner system comprising:
   a) an inverted waterproof cast sleeve comprising:
      i) an insertion end having an insertion end opening;
      ii) an extended end having an extended end opening;
      iii) a sleeve conduit extending from the insertion end opening to the extended end opening; said sleeve conduit having an inside surface and an outside surface;
   wherein the inverted waterproof cast sleeve is configured for placement over a limb with the insertion end extending around said limb and the extended end configured inverted back over the outside surface of the sleeve conduit to form a waterproof cast liner comprising:
      an outer layer of the inverted sleeve;
      an inner layer of the inverted sleeve; and
      an inverted end;
   wherein the outer layer and inner layer are configured to overlap each other to form said waterproof cast liner;
   b) a seal between the inner layer and outer layer to produce a waterproof enclosure between the inner layer and outer layer;
   c) a padding material configured within the waterproof enclosure between the outer layer and inner layer;
   d) a rigid layer configured over the outer layer to produce a waterproof cast.

13. The waterproof cast liner system of claim 12, further comprising an appendage sleeve that is contiguous with sleeve conduit and comprises:
   a) an insertion end having an insertion end opening;
   b) an extended end having an extended end opening;
   c) an appendage sleeve conduit extending from said insertion end opening to the extended end opening of the appendage sleeve; having an inside surface and an outside surface;
      wherein the insertion end opening and the extended end opening of the appendage sleeve are within the sleeve conduit; and
      wherein the appendage sleeve conduit is inverted back over a portion of an extended end of an appendage to expose said extended end of the appendage.

14. A method of making a waterproof cast, said method comprising:
   a) providing a waterproof cast liner comprising:
      i) an inverted waterproof cast sleeve comprising:
         an insertion end having an insertion end opening;
         an extended end having an extended end opening;
         a sleeve conduit extending from the insertion end opening to the extended end opening; said sleeve conduit having an inside surface and an outside surface;
   b) providing a padding material;
   c) providing a rigid material;
   d) extending the insertion end of the waterproof cast sleeve over a limb to produce a covered limb;
   e) applying said padding material over said covered limb;
   f) inverting the waterproof cast sleeve by configuring the extended end back over the covered limb to produce an inverted sleeve comprising:
      i) an outer layer of the inverted sleeve;
      ii) an inner layer of the inverted sleeve; and
      iii) an inverted end;
      wherein the padding material is configured between the outer layer and inner layer of the inverted sleeve;
   g) coupling the inner layer and outer layer of the inverted sleeve together proximal to the insertion end to produce a seal between the inner layer and outer layer and a waterproof enclosure between the inner layer and outer layer of the inverted sleeve;
      wherein the padding is configured within said waterproof enclosure;
   h) applying said rigid material over the inverted sleeve to produce a waterproof cast.

15. The method of making a waterproof cast of claim 14, wherein the seal comprises an adhesive that extends between the inner layer and the outer layer.

16. The method of making a waterproof cast of claim 15, wherein the adhesive is an adhesive tape.

17. The method of making a waterproof cast of claim 15, wherein the adhesive is a the rigid material that extends from the outer layer onto the inner layer of the inverted sleeve.

18. The method of making a waterproof cast of claim 14, wherein both the inner layer and outer layer are inverted outward over the outer layer to produce a cuff and wherein the seal is configured between the inner layer and outer layer in said cuff.

19. The method of making a waterproof cast of claim 18, wherein the cuff has an extended cuff end, and wherein the seal comprises an adhesive that extends from an outside surface of the outer layer over the extended cuff end to produce said seal.

20. The method of making a waterproof cast of claim 19, wherein the adhesive is the rigid material of the waterproof cast.

21. The method of making a waterproof cast of claim 18, wherein the waterproof cast sleeve further comprising an appendage sleeve that is contiguous with sleeve conduit and comprises:
   a) an insertion end having an insertion end opening;
   b) an extended end having an extended end opening;
   c) an appendage sleeve conduit extending from said insertion end opening to the extended end opening of the appendage sleeve; having an inside surface and an outside surface;
      wherein the insertion end opening and the extend end opening of the appendage sleeve are within the sleeve conduit; and
   wherein the method comprises inverting the appendage sleeve conduit back over a portion of an extended end of an appendage to expose said extended end of the appendage when inverting the waterproof cast sleeve.

\* \* \* \* \*